United States Patent [19]

Colodney

[11] 4,036,949

[45] * July 19, 1977

[54] CLEAR DENTIFRICE

[75] Inventor: Daniel Colodney, Piscataway, N.J.

[73] Assignee: Colgate-Palmolive Company, New York, N.Y.

[ * ] Notice: The portion of the term of this patent subsequent to Sept. 16, 1992, has been disclaimed.

[21] Appl. No.: 610,962

[22] Filed: Sept. 8, 1975

Related U.S. Application Data

[60] Continuation-in-part of Ser. No. 504,798, Sept. 10, 1974, Pat. No. 3,906,090, which is a division of Ser. No. 287,001, Sept. 7, 1972, abandoned, which is a continuation-in-part of Ser. No. 139,240, April 30, 1971, abandoned.

[51] Int. Cl.$^2$ .............................................. A61K 7/16
[52] U.S. Cl. ........................................ 424/49; 424/52
[58] Field of Search .................................. 424/52, 49

[56] References Cited

U.S. PATENT DOCUMENTS 3,711,604  1/1973  Colodney et al. ..................... 424/52

Primary Examiner—Lewis Gotts
Assistant Examiner—Cary Owens
Attorney, Agent, or Firm—Robert L. Stone; Murray M. Grill; Herbert S. Sylvester

[57] ABSTRACT

Visually clear dentifrice comprising a water-insoluble aluminosilicate sodium salt complex in which the proportion of alumina is up to 3.3% by weight and in which the mole ratio of silica to alumina is at least about 45:1, as a polishing agent having a refractive index of about 1.44–1.47 and a gel vehicle for said polishing agent having about the same refractive index as said polishing agent, said polishing agent being substantially invisible in said gel vehicle.

11 Claims, No Drawings

CLEAR DENTIFRICE

This application is a continuation-in-part of Ser. No. 504,798 filed Sept. 10, 1974, now U.S. Pat. No. 3,906,090 granted Sept. 16, 1975 whose entire disclosure is incorporated herein by reference, Ser. No. 504,798, is a Division of Ser. No. 287,001, filed Sept. 7, 1972 (now abandoned) which is a Continuation-In-Part of Ser. No. 139,240, filed Apr. 30, 1971, now abandoned.

This invention relates to dentifrices. In particular, it relates to dentifrices which are visually clear.

Dentifrices which are visually clear, i.e. transparent, are appealing to consumers. To be effective in cleaning the teeth, a polishing agent or abrasive ingredient such as calcium carbonate, dicalcium phosphate, tricalcium phosphate, calcium pyrophosphate and corresponding water insoluble magnesium salts has been included in dentifrices. An effect of such agents in convention formulations is to render the dentifrices opaque. Substantially clear dentifrices can be prepared in which water-insoluble complex salts of aluminosilicates are employed as polishing agents. Such substantially clear dentifrices have been observed to exhibit a visible haze and/or to vary in degree of cleaning or polishing effect. Typically they are alkaline and exhibit a pH of about 8-11.

It is an advantage of this invention that an effective polishing is provided while at the same time permitting the dentifrice to remain virtually transparent or clear.

A further advantage of this invention is that an aluminosilicate complex salt is provided which exhibits desirable cleaning or polishing effectiveness. Other advantages will be apparent from consideration of the following specification.

According to the present invention, there is provided a visually clear dentifrice comprising a dentally acceptable substantially water-insoluble particulate polishing agent in a gel vehicle having substantially the same refractive index as said polishing agent, said polishing agent being a synthetic amorphous complex aluminosilicate salt of sodium which contains up to 3.3% by weight of the polishing agent of alumina, and in which the mole ratio of silica to alumina is at least about 45:1, said polishing agent having a refractive index of about 1.44–1.47, up to about 20% by weight of moisture and up to about 10% by weight of sodium oxide and said polishing agent being substantially invisible in said gel vehicle.

The polishing agent employed in accordance with the invention is referred to as a complex aluminosilicate salt of sodium. It is noted that since the amount of alumina (up to 3.3%) is quite low and the amount of sodium oxide (up to 10%) may be quite low, the same material may be called a precipitated silica; its composition may fall within the limits specified for silicon dioxide in the Food Chemicals Codex. In the specification, it is generally called a complex aluminosilicate of silica since the material contains ascertainable amounts of alumina and sodium oxide.

The dentifrice may be formulated as a clear gel. The complex aluminosilicate sodium salt described above may effectively promote oral hygiene. It is an amorphous powder which further has the property that when incorporated in a gel or liquid vehicle having a refractive index of about 1.44–1.47, the particles thereof become invisible. Thus, a suitable particle size for the polishing agent is up to about 40 microns, preferably about 1–20 microns. This is the aggregate particle size.

The typical moisture content, measured by loss on ignition is about 5–20% by weight of the agent and the typical content of sodium oxide is up to about 10%, generally about 0.3–2% by weight. Typically, the agent has a loose bulk density of up to about 0.2g/cc, preferably about 0.07–0.12g/cc.

The alumina content of the salt is typically from about 0.1% to 3.3% by weight and the mole ratio of silica to alumina is typically about 45:1 to 1500:1 or more. Thus, alumina is typically present in the polishing agent bound to silica in amount of 0.1–3% and silica is similarly present in amounts of at least about 70%, amount of alumina indicated is less than that which has characterized previously employed complex sodium aluminosilicate salts used in dentifrices. When the content of alumina exceeds 3.3%, say is 3.32%, the aluminosilicate gel is often cloudy particularly when the mole ratio of silica to alumina exceeds about 45:1. It is also desirable that the complex aluminosilicate employed in the instant invention exhibit a pH in the range of 4–10, such as between about 5 and 6. The specific gravity of the complex aluminosilicate typically is about 2–3 g/cm$^3$. The polishing agent typically comprises about 5–30% by weight of the dentifrice formulation, preferably about 10–30% by weight.

The complex aluminosilicate salt appears to contain interbonded silica and alumina having Al—O—Si bonds as described by Tamele, "Chemistry of the Surface and the Activity of Alumina-Silica Cracking Catalyst," *Disc. of the Faraday Soc.* No. 8 p. 270–279 (1950) and particularly at p. 273, FIG. 1, Curve 3 wherein the interaction between silica and aluminum ions is potentiometrically detected. Further literature describing this type of complex includes Milliken et al "The Chemical Characteristics and Structure of Cracking Catalysts" *Discussions of the Faraday Society*, No. 8, Pages 279–290 (1950), and particularly the sentence bridging Pages 284 and 285. In other words, although the alumina content of the complex salt is low, the alumina which is present does not appear to be present to a substantial degree in physical mixture with silica but rather seems to be connected to the silica matrix, as by interbonding therewith. These complexes clearly differ from silica gel as is described by Plank et al, "Differences Between Silica and Silica-Alumina Gels I. Factors Affecting the Porous Structure of These Gels," *Journal of Colloid Science*, 2, Pages 399–412 (1947) and Plank, "Differences Between Silica and Silica-Alumina Gels II. A proposed Mechanism For The Gelation and Syneresis of These Gels," *Journal of Colloid Science*, 2, Pages 413–427 (1947) in which formation of the Al—O—Si bond is described at Pages 419–422.

In addition to the characteristics of the complex aluminosilicate salt indicated above, the salt may be prepared by precipitation so as to have wide ranges of surface areas, typically about 50–275 m$^2$/g (BET nitrogen absorption method); bulk densities of about 0.1–0.4g/cm$^3$; oil absorptions, typically about 15–200g. of oil per 100g. of material; and void volumes of aggregated particles of salt, typically about 105ml/gm. The pore volume or porosity of the ultimate precipitated particles may also be measured. 0.2ml/g. is a typical value.

A highly preferred grade of the complex salt is a sodium aluminosilicate having a refractive index of about 1.45–1.46 containing about 1.01% by weight of alumina and about 77–78% of silica and water measured by loss on ignition of about 5% by weight at 125° C and about 10.6% at about 1000° C and having a pH in a 4% slurry of about 7.5, a surface area of about 230–260 m²/g, a bulk density of about 0.25–0.40 g/cm³, an oil absorption of about 100–130/100 and a void volume of about 1.5–2.5ml/gm. The complex salt possessing these characteristics, in addition to providing excellent clarity to a dentifrice gel vehicle of corresponding refractive index also provides desirable cleaning properties to the dentifrice. In this type of complex salt, the precipitated particles of the salt are quite loosely distributed in a random amorphous low structure manner. Generally, when the indicated characteristics such as oil absorption are greater, such as about 179–190/100, the random amorphous distribution of particles is more compact in a higher structure manner.

A further desirable grade of the complex salt (see Example 3A below) has a refractive index of 1.46, contains 89–91% by weight silica and 0.8–1.2% by weight alumina (a mole ratio of about 150:1); 0.3–0.9% by weight sodium oxide (anhydrous); has 4–6% by weight water (as measured by loss at 105° C); and has a pH of 6.5–7.5 in 5% aqueous slurry.

The gel or liquid vehicle of the dentifrice preferably forms a toothpaste mass of a consistency which desirably can be extruded from a collapsible tube such as an aluminum tube or a lead tube. The vehicle contains liquid and solid. In general, the liquid portion comprises water, glycerine, sorbitol and the like, including suitable mixtures thereof. It is usually advantageous to use a mixture of both water and a humectant such as glycerine, sorbitol or the like. The total liquid content is generally about 20–94.5% by weight of the visually clear dentifrice, and typically includes about 0–30% by weight of water, 0- about 80% by weight of glycerine, and about 20–80% by weight of sorbitol. Preferably about 0–15% by weight of water, about 15–35% by weight of glycerine and about 30–50% by weight of sorbitol are present in the dentifrice.

In the liquid portion of the vehicle, sorbitol is suitably employed as a 70% by weight aqueous solution which has a refractive index of 1.45. Glycerine along or admixed with the sorbitol solution does not substantially alter this desirable refractive index from that of the polishing agent, since glycerine has a refractive index of 1.47. Thus, an aqueous mixture of sorbitol and a substantial mount of glycerine is eminently satisfactory to form a gel vehicle of refractive index about the same as that of the aluminosilicate complex salt which vehicle remains clear upon incorporation therein of the salt.

The solid portion of the vehicle is a gelling agent, such as the natural and synthetic gums and gum-like materials, such as Irish moss, gum tragacanth, alkali metal carboxymethyl cellulose and hydroxyethyl carboxymethyl cellulose, polyvinyl pyrrolidone, starch, water-soluble hydrophilic colloidal carboxyvinyl polymers, such as those sold under the trademark Carbopol 934 and 940 and synthetic inorganic silicated clays such as those sold under the trademark Laponite CP and Laponite SP. These grades of Laponite have the formula

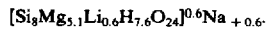

The solid portion of the vehicle is typically present in an amount up to about 10% by weight of the dentifrice and preferably about 0.5–5% by weight. When employed, grades of Laponite are preferably used in amounts of about 1–5% by weight.

Organic surface-active agents may be used in the compositions of the present invention to achieve increased prophylatic action, assist in achieving thorough and complete dispersion of the instant compositions throughout the oral cavity, and render the instant compositions more cosmetically acceptable. The organic surface-active material may be anionic, nonionic, ampholytic or cationic in nature, and it is preferred to employ as the surface-active agent a detersive material which imparts to the composition detersive and foaming properties. Suitable types of such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, olefin sulfonates, such as sodium olefin sulfonate in which the olefin group contains 12–21 carbon atoms, higher alkyl sulfoacetates, higher fatty acid ester of 1,2-dihydroxy propane sulfonates, and the substantially saturated higher aliphatic acyl amides of lower aliphatic amino carboxylic acid compounds, such as those having Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of these compounds of the present invention which are particularly advantageous since these materials exhibit a prolonged and marked effect in the inhibition of acid formulation in the oral cavity due to carbohydrates breakdown in addition of exerting some reduction in the solubility of tooth enamel in acid solutions. Another desirable material is a long chain fatty acid sodium monoglyceride sulfonate used alone or in combination with sodium lauryl sulfate.

Other particularly suitable surface-active materials include nonionic agents such as condensates of sorbitan monostearate with approximately 60 moles of ethylene oxide, condensates of ethylene oxide with propylene oxide condensates of propylene glycol ("Pluronics") and amphoteric agents such as quaternized imidazole derivatives, which are available under the trademark "Miranol" such as Miranol C₂M. Cationic surface-active germicides and antibacterial compounds such as diisobutylphenoxyethoxyethyl dime dimethyl benzyl ammonium chloride, benzyl dimethyl stearyl ammonium chloride, tertiary amines having one fatty alkyl group (of from 12–18 carbon atoms) and two (poly) oxyethylene groups attached to the nitrogen (typically containing a total of from about 2 to 50 ethanoxy groups per molecule) and salts thereof with acids, and compounds of the structure

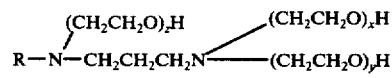

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the instant oral preparations.

Any suitable flavoring or sweetening materials may be employed in formulating a flavor for the compositions of the present invention. Examples of suitable flavoring constitutents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, perillartine and saccharine. Suitably, flavor and sweetening agents may together comprise from about 0.01 to 5% or more of the compositions of the instant invention. Chloroform may also be used.

The compositions of the present invention may also contain a suitably selected fluorine-containing compound having a beneficial effect on the care and hygiene of the oral cavity, e.g. diminution of enamel solubility in acid and protection of the teeth against decay which do not substantially detract from the clarity of the dentifrice. Examples of known fluorine com compounds include sodium fluoride, stannous fluoride, potassium fluoride, potassium stannous fluoride ($SnF_2 \cdot KF$), sodium hexafluorostannate, stannous chlorofluoride, sodium fluorozirconate and sodium monofluorophosphate. These materials, which dissociate or release fluorine-containing ions, suitably may be present in an effective but non-toxic amount, usually within the range of about 0.01 to 1% by weight of the water-soluble fluorine content thereof. Sodium fluoride and sodium monofluorophosphate are particularly preferred for inclusion in clear gel dentifrices, as well as mixtures thereof. The level of retention of fluoride-containing ion with sodium monofluorophosphate is particularly high.

Various other materials may be incorporated in the oral preparations of this invention. Examples thereof are colouring or whitening agents or dyestuffs, preservatives, silicones, chlorophyll compounds, ammoniated materials such as urea, diammoniumphosphated and mixtures thereof, and other constituents.

The adjuvants are incorporated in the instant compositions in amounts which do not substantially adversely affect the properties and characteristics desired and are selected and used in proper amounts depending upon the particular type of preparation involved.

Antibacterial agents may also be employed in the oral preparations of the instant invention in an amount of about 0.01-5% by weight. Typical antibacterial agents include $N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-chlorophenylbiguanidohexane;
1,6-bis-(2-ethylhexylbiguanido)hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine and their non-toxic acid addition salts.

Synthetic finely divided silicas such as those sold under the trademarks Cab-O-Sil M-5, Syloid 244, Syloid 266 and Aerosil D200 and mixtures thereof may also be employed in amounts of about 0.5-20% by weight to promote thickening or gelling of the dentifrice.

In the manufacture of dentifrices, it is conventional to remove entrained air from the product by deaeration under vacuum typically at a late stage in the manufacture. In an aspect of the instant invention, it has been observed that in clear dentifrice gels of suitable viscosity, the dispersed, immobile air bubbles desirably enhance the appearance of the dentifrice, and can therefore, be permitted to remain. Furthermore, air can be at least partially removed and reintroduced in small substantially globular or spheroidal bubbles of say about 0.1-8mm in size, well distributed in the gel at an average of at least about one per cubic centimeter. Such air bubbles may be placed in the gel by stirring it while introducing the air. Instead of air, bubbles of another gas, such as nitrogen or carbon dioxide, can be introduced in non-toxic quantity.

In particular, carbon dioxide can provide an effervescent character to the dentifrice.

In the event it is desired to have a minimum amount of air in the dentifrice, or only to have to remove a minimum amount of air from the dentifrice of the instant invention, the "Unimix" apparatus described in "Process Engineering," Sept. 11, 1970, Pages 81-85, is particularly efficacious for this purpose. In this apparatus a mixing tool can be rotated in clockwise or followed by the action of a scraper clean. Preferably, a plastic such as polytetrafluorethane is used as the scraper since it is compatible with the various ingredients of the dentifrice. The positioning of the mixing tool and the scraper from a raised central column in the apparatus and the further presence of a hydraulically operated vacuum tight lid permits but little air to enter the formulation during processing. Thus, gelling agent and a portion of liquid are blended, then the remaining liquid can be separately blended with the polishing agent and additional components (except for post-added components, such as flavoring oil) in the Unimix, and then the two dispersions blended together in the Unimix apparatus. If desired, the small amount of air can be largely removed under the depressurized conditions in the apparatus. The apparatus can be used to blend ingredients at room temperature, as well as at higher temperatures.

Furthermore, if desired, visible particles of dyes, pearlescent flakes or particles of insoluble salts of antibacterial agents such as the disarcosinate salt of 1,6-di-p-chlorophenylbiguanidohexane, as well as other particles, can be distributed in the dentifrice.

The dentifrice should have a pH practicable for use. A moderately acid, neutral or moderately alkaline pH is preferred.

The following specific examples are further illustrative of the nature of the present invention, although it is understood that the invention is not limited thereto. All amounts are by weight unless otherwise indicated.

EXAMPLE 1

The following dentifrices are prepared and entrained air is removed under vacuum:

| Component | Parts |
| --- | --- |
| Sorbitol (70% solution) | 45.4 |
| Glycerine | 25 |
| Sodium carboxymethyl-cellulose | 0.7 |
| Syloid 244 | 5 |
| Sodium aluminosilicate (as indicated) | 16 |
| Sodium layryl sulfate | 2 |
| Sodium benzoate | 0.5 |
| Sodium saccharine | 0.2 |
| Color | 0.2 |
| Flavor and chloroform | 2.0 |

-continued

| Component | Parts |
|---|---|
| Water | 3 |

The following grades of sodium aluminosilicate were employed:

| | Sodium Aluminosilicate Grade | | | | |
|---|---|---|---|---|---|
| | A | B | C | D | E |
| Index of Refraction | 1.46 | 1.46 | 1.46 | 1.46 | 1.46 |
| %Al$_2$O$_3$(anhydrous) | 3.32 | 4.10 | 8.2 | 3.22 | 0.1 |
| %SiO$_2$ (anhydrous) | 86.76 | 86.03 | m72 | 88.22 | 88.65 |
| Mole Ratio SiO$_2$:Al$_2$O$_3$ | 44.4:1 | 36.75:1 | 15:1 | 47.4:1 | approx. 1500:1 |
| % Na$_2$O (anhydrous) | 0.84 | 1.17 | 7 | 0.50 | — |
| % H$_2$O (by loss upon ignition) | 4.42 | 6.20 | 6 | 7.71 | 8.6 |
| pH (5g/395 ml H$_2$O for 5 minutes) | 9.9 | 5.2 | 10.5 | 4.3 | 5.4 |

Dentifrices prepared with the sodium aluminosilicate complex grades D and E are visually clear and transparent gels and exhibit good polishing effect on dental enamel. Dentifrice prepared with complex Grades A and B exhibit a haze which render the gels more translucent. This haze is also noted in some gels prepared with Grade C. Cleaning and polishing of dental enamel with the dentifrices containing Grades D and E is more effective than with Grade C.

Sodium monofluorophosphate is also satisfactorily incorporated in Dentifrices D and E in amount of 0.76 parts.

EXAMPLE 2

A dentifrice containing 44.4 parts of 70% sorbitol, 6 parts of Syloid 244, 16 parts of sodium aluminosilicate and other components and amounts as indicated in Example 1 is prepared in which the sodium aluminosilicate contains 77.24–78% silica and 1.01% alumina (a mol ratio of silica to alumina of more than 130:1) and in which 5% water is lost on ignition at 125° C and in which 10.6% water is lost on ignition at about 1000° C. The pH of a 4% aqueous slurry of the sodium aluminosilicate is 7.5, its surface area is about 250–260 m$^2$/g and its average pore volume is 0.185 ml/g.

The dentifrice is visually very clear and transparent. The polishing agent provides a highly satisfactory degree of dentin abrasion.

The aluminosilicate employed has a low structure aluminosilicate. Its oil absorption capability is about 100–130g of the oil per 100g of salt is employed.

EXAMPLE 3

The following dentifrices are prepared, deaerated and tubed:

| | PARTS BY WEIGHT | | | |
|---|---|---|---|---|
| COMPONENTS | A | B | C | D |
| Glycerine | 25 | 25 | 25 | 25 |
| Sodium carboxymethylcellulose | 0.35 | | 0.35 | 0.35 |
| Sodium Benzoate | 0.5 | 0.5 | 0.5 | 0.5 |
| Sodium Saccharine | 0.17 | 0.17 | 0.17 | 0.17 |
| Color (1% solution) | 0.7 | 0.7 | 0.7 | 0.7 |
| Polyethylene glycol 600 | 3 | 3 | 3 | 3 |
| Water | 3 | 3 | 3 | 3 |
| Sorbitol (70%) | 33.28 | 33.63 | 45.28 | 45.28 |
| Sodium Aluminosilicate* | 30 | — | 5 | — |
| Sodium Aluminosilicate** | — | 30 | — | 5 |
| Flavor | 1 | 1 | 1 | 1 |
| Syloid 244 (Silica Gel) | — | — | 13 | 13 |
| Sodium Lauryl Sulfate | 2 | 2 | 2 | 2 |
| Chloroform | 1 | 1 | 1 | 1 |

*The sodium aluminosilicate employed in dentifrice A and C had a refractive index of 1.46; contained 89–91% silica; 0.8–1.2% alumina (a mole ratio of about 150:1); 0.3–0.9% sodium oxide (anhydrous); 4–6% water is lost at 105° C; the pH of a 5% aqueous slurry is 6.5–7.5.
**The sodium aluminosilicate employed in dentifrices B and D had a refr. index of 1.46; contained 70–74% silica and 8–9.5% sodium oxide (anhydrous); 4–7% water is lost a 105° C; and the pH of a 5% slurry is 9.5–11. (The mole ratio of silica to alumina was about 16:1 or less).

Dentifrice A possesses excellent clarity upon visual examination while Dentifrice B is transparent but hazy and less clear. The clarity differences between Dentifrices C and D are less marked, but Dentifrice C does possess better clarity than Dentifrice D.

Thus, the clarity improvement for dentifrices containing sodium aluminosilicate in accordance with this invention begins to be noticeable at a level of 5% sodium aluminosilicate and becomes greater as greater amounts of the sodium aluminosilicate is used.

It will be apparent to one skilled in the art that various modifications of the above examples may be made thereto.

I claim:

1. A visually clear dentifrice comprising about 5–30% by weight of a dentally acceptable substantially water-insoluble particulate polishing agent in a gel vehicle having substantially the same refractive index as said polishing agent, said polishing agent being a synthetic amorphous complex alumino-silicate salt of sodium which contains about 0.1 to 3.3% by weight of the polishing agent of alumina, and in which the mole ratio of silica to alumina is about 45:1 to 1500:1 said polishing agent having a refractive index of about 1.44–1.47, about 5 to 20% by weight of moisture and up to about 10% by weight sodium oxide and said polishing agent being substantially invisible in said gel vehicle.

2. The visually clear dentifrice claimed in claim 1 wherein said polishing agent is present in amount of about 10–30% by weight.

3. The visually clear dentifrice claimed in claim 2 wherein the silica content is at least about 70% by weight.

4. The visually clear dentifrice claimed in claim 1 wherein said dentrifrice contains about 25–80% by weight of glycerine and about 30–50% by weight of sorbitol as the liquid portion of said gel vehicle and about 1–5% by weight of a gelling agent as the solid portion of said gel vehicle.

5. The visually clear dentifrice claimed in claim 4 wherein said gelling agent is sodium carboxymethyl cellulose.

6. The visually clear dentifrice claimed in claim 1 wherein said dentifrice includes about 0.5–20% by weight of a synthetic finely divided silica thickening agent.

7. The visually clear dentifrice claimed in claim 1 wherein said dentifrice contains sodium monofluorophosphate.

8. A dentifrice according to claim 1 wherein the alumino-silicate salt has a refractive index of about 1.45–1.46.

9. A dentifrice as in claim 7 in which said alumino-silicate salt has a particle size in the range of 1 to 20 microns.

10. A dentifrice as in claim 3 in which said sodium alumino silicate has an oil absorption value of up to about 130 g. per 100 g.

11. The visually clear dentifrice claimed in claim 1 wherein the amount of sodium oxide in said aluminosilicate salt is about 0.3 to 2% by weight.

* * * * *